United States Patent [19]
Scholander et al.

[11] Patent Number: 5,840,190
[45] Date of Patent: Nov. 24, 1998

[54] SURFACE MODIFIED BIOCOMPATIBLE MEMBRANES

[75] Inventors: Elisabeth Scholander, Upsala, Sweden; Andrzej Werynski; Andrzej Jozwiak, both of Warsaw, Poland; Olle Larm, Bromma, Sweden

[73] Assignee: Norsk Hydro A.S., Oslo, Norway

[21] Appl. No.: 557,066

[22] PCT Filed: May 9, 1994

[86] PCT No.: PCT/NO94/00088

§ 371 Date: Feb. 1, 1996

§ 102(e) Date: Feb. 1, 1996

[87] PCT Pub. No.: WO94/26399

PCT Pub. Date: Nov. 24, 1994

[30] Foreign Application Priority Data

May 19, 1993 [NO] Norway ..................................... 931809

[51] Int. Cl.$^6$ .................................................. B01D 39/00
[52] U.S. Cl. ................................ 210/500.24; 210/500.27; 210/500.29; 210/500.3; 210/500.41; 210/500.43; 204/4; 204/49
[58] Field of Search ........................... 210/500.3, 500.34, 210/500.37, 500.41, 500.43, 500.24, 500.29, 500.38, 500.27; 264/41, 49

[56] References Cited

U.S. PATENT DOCUMENTS

| | | | |
|---|---|---|---|
| 3,441,142 | 4/1969 | Oja | 210/500.1 |
| 3,522,346 | 7/1970 | Chang | 210/500.1 |
| 3,616,935 | 11/1971 | Love et al. | 210/500.1 |
| 3,705,084 | 12/1972 | Reynolds | 195/63 |
| 4,102,746 | 7/1978 | Goldberg | 210/6 |
| 4,702,840 | 10/1987 | Degen | 210/638 |
| 4,855,234 | 8/1989 | Hendricksorl et al. | 435/181 |
| 4,906,375 | 3/1990 | Heilmann | 210/500.23 |
| 5,041,225 | 8/1991 | Norman | 210/500.36 |
| 5,283,186 | 2/1994 | Cunningham et al. | 435/180 |
| 5,420,047 | 5/1995 | Brandt et al. | 435/7.9 |
| 5,476,665 | 12/1995 | Dennison | 424/484 |

FOREIGN PATENT DOCUMENTS

| | | |
|---|---|---|
| 0 086 186 | 8/1983 | European Pat. Off. . |
| 0 497 185 | 8/1992 | European Pat. Off. . |

*Primary Examiner*—Ana Fortuna
*Attorney, Agent, or Firm*—Wenderoth, Lind & Ponack, L.L.P.

[57] ABSTRACT

A surface modified biocompatible membranes used in contact with body fluids or tissue and method of preparing the membrane with functional groups incorporated into the membrane material to covalent bond compounds that infer biocompactibility to the surface.

14 Claims, No Drawings

SURFACE MODIFIED BIOCOMPATIBLE MEMBRANES

The present invention concerns biocompatible membranes and a method for the incorporation of functional groups into polymer membranes for immobilisation of bioactive molecules.

TECHNICAL FIELD

In recent years, great progress has been made in the development of medical devices for treatment of various disorders, and in the development of permanent implants to replace pans of the human body. When in use, many of these devices or implants have contact with blood for short periods of time or permanently.

Oxygenators used in heart-lung machines and hemofiltration modules used for blood purification of patients with renal insufficiencies are examples of membrane containing devices used in extracorporeal circulation of blood. These devices have large surface areas, and when used, the blood-exposure is substantial. The need for blood-compatible surface treatments for these devices is therefore obvious. Other examples of membrane containing devices are invasive blood-gas sensors and artificial organs such as artificial pancreas and artificial skin.

It is known that chemical entities having a biological activity may be bound to the surface of a substrate to improve the blood-compatibility of the substrate, if functional groups are made available on the substrate surface by surface modification. Such functional groups on the substrate surface may be charged for ionic interaction or react covalently with functional groups on the chemical entity.

PRIOR ART

When blood is exposed to artificial surfaces, several of the organism's defence systems, such as the coagulation, complement and immune systems are activated. These systems are believed to be interrelated through common intermediates. To avoid activation of the coagulation system in short time exposure of blood to foreign materials, heparin is administered systemically. It is used routinely but has several side-effects such as bleeding, thrombocytopenia or osteoporosis. Sometimes it is only partially effective, resulting in fibrin deposition on the foreign material, which leads to improper function of the device. Patients who receive blood-contacting permanent implants often have to depend on life-long anticoagulation therapies requiring frequent laboratory monitoring.

Many attempts have been made to modify surfaces of foreign materials to render them more biocompatible. A negatively charged surface is believed to give less platelet adhesion, but on the other hand enhances coagulation contact activation. The opposite has been noted for positively charged surfaces. Synthetic hemofilter membrane materials are regarded as more biocompatible, with respect to activation of the complement system, than the cellulose-based membranes. The synthetic membranes on the other hand are often hydrophobic, with high protein adsorption and sometimes inferior filtration properties. Hydrophobic surfaces are also known to promote platelet adhesion.

Biologically active surfaces, i. e. surfaces with immobilised compounds that actively participate, on a molecular level, in the process of preventing activation of the defence systems in the contact between foreign materials and body fluids or tissue, can be prepared by end-point attachment of heparin to device or implant materials surfaces, as described in Larm et al. EP-86186B1. These heparin-modified surfaces show much improved biocompatibility, both with respect to coagulation and complement activation.

Device or implant materials surfaces are generally of low reactivity, and functional groups must be introduced for coupling of bioactive reagent(s) to these surfaces. This can be achieved by coating the materials surfaces with compounds containing the proper functional groups (EP-86187B2), chemical grafting of reactive compounds (D. E. Bergbreiter in Chemically Modified Surfaces H. A. Mottola and J. R. Steinmetz (Eds) 1992 Elsevier Science publishers p.133–154.), plasma treatment with reactive monomers or gases (H. Yasuda, Plasma Polymerization, Academic Press 1985), or, in some cases, chemical reactions of the device materials to introduce functional groups (D. E. Bergbreiter in Chemically Modified Surfaces H. A. Mottola and J. R. Steinmetz (Eds) 1992 Elsevier Science publishers p.133–154.). To functional groups generated by any of these methods, biologically active reagents can be coupled by conventional chemical methods, to provide ionically or covalently bonded biologically active compounds on the materials surfaces.

Any method for pre treatment of a materials surface for the immobilisation of biologically active compounds must fulfill the following criteria:

The pre treatment must generate functional groups that are well anchored into the underlying material, so that compounds containing functional groups do not leak out into the blood-stream on use.

The functional groups must be present in sufficiently large amounts to allow coupling of an adequate number of bioactive molecules.

The functional groups must be exposed on the material surface to be available for coupling of bioactive compounds.

The properties of the bulk material should not be altered unfavourably.

Most methods of generating functional groups for immobilisation of bioactive compounds have draw-backs with respect to the criteria above. Coating the material surfaces with functional compounds often result in coatings with poor adherence to the substrate surface. Plasma treatment or activation for chemical grafting is not possible on all device geometry's, e.g. the inside of hollow-fibres. Direct chemical treatment of a material surface often requires harsh chemical reaction conditions and is thus limited to a few device materials. Not all pre treatment methods generate sufficient amounts of functional groups, and consequently the amounts of immobilised bioactive compound is not sufficient to accomplish biocompatibility.

When treating a device incorporating a membrane, the physical properties of the membrane-material such as pore-size, clearance of water, and passage of molecules of a certain size has to be taken into consideration. Several of the pre treatment methods described above would alter the physical properties of a membrane, or even block the pores of said membrane.

By producing the biocompatible surfaces according to the present invention the above mentioned draw-backs of the prior art are avoided.

A polymer-membrane can be made by the phase inversion technique by precipitating a solution of the membrane forming polymer in a non-solvent, normally water (W. Pusch and A. Walch, Angew. Chem. Int. Ed. Engl. 21 (1982) p.660–685). A casting solution for membrane-formation is composed of a membrane-forming polymer e.g. cellulose, cellulose acetate or other cellulose derivatives, polysulfone, polyacrylonitrile or any other membrane-forming material in a solvent or mixture of solvents. As a solvent dimethylacetamide, dimethylsulfoxide, acetone, dimethylformamide, formarnmide, N-methylpyrrolidone, cyclohexanone, organic and inorganic acids or mixtures thereof as well as other solvents may be used. It is also possible to add a small amount of a non-solvent for the membrane-forming polymer to the solvent or mixture of solvents, provided that the whole mixture remains a solvent for the polymer.

A coagulation bath containing a non-solvent for the membrane-forming polymer coagulates the casting solution and forms the membrane. The coagulation bath may be a mixture of non-solvent and a small amount of solvent.

A hollow fibre membrane is formed by means of a spinneret arranged in the form of a tube in an orifice. From said spinneret two streams are exerted, one stream consists of a spinning solution comprising the membrane forming polymer extruded through the ring shaped orifice, and the second stream consists of a core liquid extruded through the central tube.

The core liquid and coagulation bath contain a non-solvent for the membrane forming polymer and both take part in coagulation of the spinning solution and formation of the membrane. (H. I. Mahon and B. J. Lipps, Encyclop. Polym. Sci. Technology, 15 (1971) p.258–272). The core liquid may also be an oil that is immiscible with the polymer solution and coagulation bath and is inert towards them, like isopropyl myristate.

In EPA-0090483 and EP 87 228 B2, a method for the surface modification of skinless, microporous polyamide membranes is described, where a surface modifying polymer of molecular weight above 20 000 with functional groups (amino, hydroxyl, carboxylic sulfonic acids or others) is added to the casting solution in proportions around 1% based on the weight of the polyamide resin. When the membrane is precipitated in a coagulation bath being a non-solvent for polyamide, the surface modifying polymer becomes an integral part of the membrane, mainly exposed on the surface of the membrane. The surface modifying polymer increases the hydrofilicity of the membrane and may give the membrane an unusual zeta-potential versus pH-profile. These properties allows for selective particle removal, eg negative particles can be removed by a positively charged membrane according to this patent. Other useful properties of these membranes are the ability to remove dissolved metal contaminants by complex formation, e.g. from liquids for recovery of precious metals in the plating industry, or after further modification of the modified membranes to impart affinity for certain biological compounds, in the processing of biological or biochemical preparations, such as in the removal or isolation of biological or pharmaceutical materials for preparation of substances in the pharmaceutical industry. Another application of these membranes are the immobilisation of enzymes for food processing or preparation of pharmaceuticals. The immobilised enzymes provides convenient ways of separating the enzyme from the product after reaction, as well as means for simultaneous removal of particular contaminants such as cell debris, a common contaminant in the commercial enzyme preparations.

In EP-0090483A and EP-087228B2, neither medical applications such as use in medical devices or implants, nor improved biocompatibility of the surface modified membranes are mentioned.

SUMMARY OF THE INVENTION

The present invention concerns surface modified biocompatible membranes used in contact with body fluids or tissue and a method of preparing polymer surface modified biocompatible membranes with functional groups incorporated into the membrane material thus to immobilize compounds that confer biocompatibility to the surface, where the incorporation of the surface modifying polymer takes place during formation of the membranes and the physical properties of the membranes are not affected by immobilisation of the bioactive molecules. This can be achieved by the A or B method or variations or combinations thereof.

Method A i) Preparation of a casting solution containing the membrane forming polymer.

ii) Precipitating the membrane from the casting solution into a coagulation bath containing the surface modifying polymer.

or

Method B i) Preparation of a casting solution containing the membrane forming polymer and the surface modifying polymer.

ii) Precipitating the membrane from the casting solution into a coagulation bath.

The invention can be used on any polymeric material used for medical devices that are prepared by casting, spinning or similar methods. Examples of such medical devices other than membrane-containing devices are implants such as vascular grafts, stents, pacemaker leads, sutures or implantable catheters or disposable articles such as various catheters, sensors or wound dressings.

DETAILED DESCRIPTION OF THE INVENTION

Method A

A casting solution is prepared by dissolving the membrane forming polymer, to be choosen from cellulose, cellulose acetate, polysulfone, sulfonated polysulfone, polyamide, polyacrylonitrile, polymethylmethacrylate, other membrane forming polymers or other derivatives thereof. The solvent is dimethylacetamide, dimethylsulfoxide, actone, dimethylformamide, formamide, organic or inorganic acids or mixtures thereof. It is also possible to add a small portion of a non-solvent, provided that the whole system remains a solvent for the polymer. The concentration of the membrane forming polymer is preferably between 15 and 30%, more preferably between 20 and 28%, the most preferred concentration being 25%.

The membrane is precipitated from the casting solution in a non-solvent, typically a hydrophilic solvent, preferably water, possibly with a small amount of added solvent for the membrane forming polymer. The surface modifying compound is dissolved in this mixture of non-solvent and solvent at a concentration typically between 0.5 and 10%, more preferably between 0.5 and 4%, most preferably 1% . The surface modifying compound is, on precipitation, incorporated into the surface of the membrane. The surface modifying compound is selected from the group of organic compounds carrying functional groups such as amino, hydroxyl, carboxylic acid, carboxylic acid anhydride, isocyanate, epoxy, carbodiimido, sulfonic acid or other reactive functional groups. The functional compounds could be polymers e.g. polyamines such as polyethylenimine (PEI) or polylysine, polycarboxylic acids like polyacrylic acid, polyalcohols like polyvinyl alcohol or polysaccharides, polyanhydrides, polyisocyanates, polyepoxides, polycarbodimide or other functional polymers. The functional compounds could also be lower molecular weight compounds that by some affinity other than entanglement, (covalent, ionic or Van deer Waals-bonds), sticks to the surface of the membrane. Typically the surface modifying compound is a polymeric amine with molecular weight above 25000, preferably a polyethyleneimine.

The precipitated surface modified membrane is carefully rinsed with water, and then reacted with a bioactive compound and a coupling agent.

The bioactive reagent can be coupled by conventional coupling techniques to the functional groups on the membrane surfaces. To, e.g., a membrane surface containing amino groups, amine containing compounds such as proteins can be coupled by, e.g., a dialdehyde such as glutardialdehyde. Carboxylic acid ligands can be coupled after activation with a water-soluble carbodiimide e.g. 1-ethyl-3-(3-dimethylaminopropyl)-carbodiimide hydrochloride (EDC). Hydroxylic compounds can be coupled to an aminated surface that has been activated by bisepoxiranes or a carbonyldiimidazol. A surface containing carboxylic acid groups can be activated for coupling of amino groups or hydroxyl groups by treatment with EDC. Anhydrides on a membrane surface can be converted to aminogroups by treatment with diamines, or hydrolysed to carboxylic acid groups. To isocyanates, epoxides or carbodiimides on the surface, bioactive compounds containing amino or hydroxy groups can be coupled.

A bioactive compound on a membrane surface confers biocompatibility to the surface by interacting with the defence systems of the body in order to prevent activation, or to inactivate compounds created in such defence reactions. The bioactive compound to be coupled to the surface is selected from the group glycosaminoglycans typically heparin, other anticoagulant agents like hiruidin, prostaglandins, antithrombins or thrombolytic or fibrinolytic agents like streptokinase, urokinase or tissue plasminogen activator (tPA), or other compounds or mixtures thereof that by some mechanism actively affect the defence systems of the living body. The biocompatibility of surface immobilised heparin is well documented, and heparin is therefore preferred as bioactive compound.

Heparin can be coupled to an aminated surface by multi-point or end-point attachment. Multi-point attachment is achieved by using any of the reagents described above to couple the free amino-groups, carboxylic acid groups or hydroxyl groups of heparin to an aminated surface. Heparin covalently coupled by end-point attachment with maintained biological activity of the heparin molecule is preferred to render the membranes biocompatible. End point attachment of heparin is obtained by coupling partly degraded heparin (nitrous acid) containing terminal free aldehyde groups. With polyethyleneimine as the surface modifying agent, the coupling agent is a reducing agent, capable of reducing the Schiffs bases formed between the end-positioned aldehyde groups of the modified heparin and the amino-groups on the membrane surface. Preferably this reducing agent is sodium cyanoborohydride (EP-86186B2). The resulting biocompatible (heparin-coupled) membrane is carefully rinsed to remove uncoupled heparin.

Heparin or other negatively charged bioactive compounds can also be immobilised to an aminated surface by ionic attachment by first transferring the aminated surface into a positively charged form, or quartinizing the amino-groups on the surface and then treating the positively charged surface with a solution of heparin.

Method B

The surface modifying compound is added to the casting solution which is prepared as in Procedure A, at a concentration varying between 0.5 and 10%, more preferably between 0.5 and 4% and most preferably 1%. The surface modifying polymer is choosen from the group mentioned in alternative A, but with the limitation that it must be soluble in the casting solution. The membrane is precipitated in a non-solvent as described above. Also in this procedure, the surface modifying polymer will be directed to the surface of the membrane as a consequence of the more hydrophilic nature of the surface modifying polymer.

A bioactive agent is then coupled to the surface modified membrane as described in method A.

The present invention provides a method of preparing biocompatible membranes for use in hemofiltration and other blood purification treatments. By incorporating functional polymers, preferably polymeric amines in the membrane at the production of said membranes, and immobilising heparin by means of the amino-groups, membranes with improved blood-compatibility compared to the corresponding membranes without immobilised heparin are obtained. As the functional compounds are incorporated in the production of the membranes, and not in a reaction step afterwards, the physical properties of the membrane such as pore size, clearance of water and passage of molecules of a certain size, can easily be controlled. Another advantage of the present invention is that the coupling of heparin can be performed in one step, as functional groups are present on the membrane surface.

EXAMPLES

The following non-limiting examples further illustrate the invention.

EXAMPLE 1

Preparation of Aminated Cellulose Acetate Membranes according to Method A.

A casting solution was prepared by dissolving 25 g of cellulose acetate (Eastman CA-398-10 USP grade) in 75 g of mixture of dimethylformamide and formamide in ratio 5:1 respectively. 1 cm$^3$ of the casting composition was spread out on a clean glass plate and then immersed into a coagulating bath, which is a 1% water solution of Polymin SN (BASF). The aminated membranes were kept in the bath for several minutes to set, washed extensively with water, immersed in a 15% glycerol solution in water for 1 hour and dried at ambient conditions.

EXAMPLE 1a

Heparinisation of Aminated Cellulose Acetate Membranes.

Heparin was covalently coupled to the flat sheet aminated membrane from example 1 by keeping the membrane in a solution of partially nitrous acid degraded heparin, essentially prepared as described in EP-86186, (25 mg) in water containing sodiumcyanoborohydride (2.5 mg) and sodium chloride (880 mg) at pH 3.9 and 50° for 2 hours. The heparinised membrane was extensively rinsed with water, borate buffer pH 9 and water, to remove non covalently bound heparin. The amount of surface-immobilised heparin as measured by the method described by Riesenfeld and Roden, Anal. Biochem. 188 (1990) p.383–389, and corrected for background values, was 2.8 $\mu g/cm^2$.

Membranes of cellulose acetate, were prepared as described as in Example 1, but omitting the addition of PEI or other functional polymers. These membranes were treated with heparin as described above. No surface bound heparin could be detected.

EXAMPLE 2

Preparation of Aminated Polysulfone Membranes according to Method A.

20 g polysulfone (Udel polysulfone P3500 Natural 11, AMOCO, molecular weight 45000) was dissolved in 80 g of a mixture of dimethylacetamide and polyvinylpyrrolidone in the ratio 6:2 and processed as in Example 1. Heparinisation of the membrane according to Example 1a yielded a heparinised membrane with a surface density of 1.0 $\mu$g heparin/$cm^2$. Membranes of polysulfone were prepared as described above, but omitting the addition of PEI or other functional polymers. These membranes were treated with heparin as described above. No surface bound heparin could be detected.

EXAMPLE 3

Preparation of Aminated Cellulose Acetate Membranes according to Method B.

Example 1 was repeated, but to the casting solution Polymin P (BASF,1%) was added, and the coagulation bath was water. Heparinisation of the membrane according to example 1a yielded a heparinised membrane with a surface density of 8.8 $\mu$g heparin/$cm^2$.

EXAMPLE 4

Preparation of Aminated Polysulfone Membranes according to Method B.

Example 2 was repeated, but to the casting solution Polymin P (1%) was added, and the coagulation bath was water. Heparinisation of the membrane according to example 1$a$ yielded a heparinised membrane with a surface density of 2.9 $\mu$g heparin/$cm^2$.

Examples 1–4 shows that amino-groups are available for coupling of substantial amount of heparin on the surfaces of the membranes prepared according to the present invention.

EXAMPLE 5

Leakage Test of Heparinised Membranes.

The heparinised membranes from example 3 and 4 were treated with a solution of albumin for 24 hours, thoroughly rinsed with water and assayed for heparin. The heparin content was 7.6 and 2.8 $\mu$g/$cm^2$ respectively indicating minimal or no leakage of the immobilised heparin.

EXAMPLE 6

Preparation of Cellulose Acetate Membranes containing Anhydrido Groups according to Method B.

Example 1 was repeated, but the casting solution contained polymaleic anhydride (1%, Polysciences Inc.). The coagulating bath was water containing 1,3-diaminopropane (1%w/w). Heparinisation of the membrane according to example 1$a$ yielded a heparinised membrane with a surface density of 1.9 $\mu$g heparin/$cm^2$.

EXAMPLE 7

Preparation of Aminated Cellulose Acetate Hollow Fibre Membranes according to Method A.

A spinning solution was prepared by dissolving 25 g of cellulose acetate in 75 g of a mixture of dimethylformamide and formamide in a of ratio 5:1 respectively. This spinning solution was injected at the rate of 4 $cm^3$/min into the ring shaped orifice of a spinneret (internal diameter of the ring: 0.3 mm, external diameter of the ring 0.5 mm). The spinneret was placed 2 cm above the coagulating bath (water). Through the tube positioned in the centre of the orifice (outer diameter of the tube 0.3 mm, inner diameter of the tube 0.15 mm) the core liquid, which is a 1% water solution of Polymin SN, is pumped. The nascent hollow fibre moves through the coagulating bath at the rate of 9 m/min; from the outlet of coagulating bath the hollow fibre is guided to the washing bath and after that it is wound on a wheel rotating in second washing bath The hollow fibres were cut in bundles, immersed in 10% solution of glycerol for several hours and then dried and closed in plastic housing of the type commonly used for dialysis units but of length 6 cm and 1 cm in diameter The surface area of the membrane was 36 $cm^2$.

EXAMPLE 8

Heparinisation of Aminated Hollow Fibres.

A hollow fibre dialysis unit, prepared according to example 7, was heparinised essentially according to example 1a. To obtain heparin surface coating on end-caps and glue-surfaces, they were treated with Polymin SN in water, essentially as described in EP 0086 187B2 before assembling and heparinising the hemofiltration unit. Amount surface bound heparin on the fibres of the heparinised unit was 3.6 $\mu$g/$cm^2$.

This example demonstrates heparin can be coupled to hollow fibres prepared according to the present invention.

EXAMPLE 9

Blood Compatibility Test of Heparinised Hollow Fibre Filtration Modules (rat).

Hollow fibre minimodules were prepared according to example 7 to obtain minifilters of a size suitable for experiments in rats. The minifilter units were heparinised according to Example 8. The coagulation compatibility of the filters was evaluated in a rat model using blood pressure drop over the filter as a measure of coagulation (clot formation) in the filter. Sprague-Dawley rats weighing 325–420 g were anaesthetised with Inactin (Thiobarbiturat 120 mg/kg body weight). Heparinised polyethylene catheters (heparinised essentially as described in EP 0086 187 B2) were inserted in v. jugularis sin and a. carotis dx. The catheter from a. carotis dx. was connected to a peristaltic pump (Ismatec Mölnlycke, Sweden) calibrated to give a blood flow of 2.0 ml/min. A minifilter unit was connected to the pump and to the catheter inserted into v. jugularis sin. The filtrate side of the filter module was filled with saline and the filtrate ports were closed. Gould P 23 ID transducers for pressure measurements were connected to the extracorporeal blood circuit immediately before and after the filter module and pressure drop over the filter was continuously monitored using a Grass Polygraf model 7A. All blood contacting tubings and connectors in the circuit were heparinised essentially according to EP 0086 187 B2. No heparin was injected systemically.

The pressure difference over the minifilters with fibres according to the invention was constant at 10–30 mm Hg (indicative of insignificant activation of coagulation) for 50–75 minutes (typically 60 minutes) whereafter an abrupt increase in the pressure up to 400 mm Hg occured, indicating clot formation in the filter-module and the experiment was interrupted.

Control experiments using the described rat model were performed with minifilters made up from hollow fibres prepared according to Example 7, but excluding Polymin SN in the core liquid and omitting the heparinisation procedure described in Example 8. The pressure difference over the filters immediately started to increase after initiation of the rat experiment indicating immediate activation of coagulation and clot formation. Typical values were 50, 100 and 150–200 mm Hg at 10, 15 and 20 minutes respectively after start of the experiments. After 40–50 minutes the pressure difference was 400 mm Hg indicating extensive clot formation in the filter module.

After the experiment, the filter modules were dismounted, rinsed with saline and inspected. Clot formation was observed mainly in the entrance ports, but also in the outlets of both the control filter and the filter with fibres prepared according to the present invention. Rinsing of the blood in the control fibres with saline could not be performed due to massive clot formation in fibres. The blood in the fibres prepared according to the present invention was readily rinsed with saline and after rinsing no sign of clot formation in the fibres could be observed.

Blood samples were taken from the rat immediately before, 1.5 and 10 minutes after initiation of the experiment and immediately after the experiment. The citrated blood samples were immediately centrifuged to obtain platelet poor plasma that was stored at −20° C. until analysis. The plasma samples were analysed for heparin activity using an assay based on inhibition of thrombin. The assay utilises the chromogenic substrate S-2238 (Chromogenix, Mölndal, Sweden) and has a detection limit of 0.02 IU/ml. (M ätzsch, T. et al., Blood Coagulation and Fibrinolysis, 1991, 2, 651–657). No heparin activity could be detected in any of the plasma samples thereby demonstrating the in vivo stability of the heparin bonding according to the present invention. It further demonstrates that the improved performance of the heparinised filters is not due to leakage of heparin into the blood circulation but caused by improved biocompatibility attributable to the present invention.

EXAMPLE 10

Blood Compatibility Test of Heparinised Hollow Fibre Filtration Modules (pig).

Full size hollow fibre modules with a surface area of 0.73 $m^2$ were prepared according to example 7. For the experiment, a pig with body weight of 37 kg was used. In both groins of the animal, 10 Fr polyurethane catheters were inserted into the femoral artery and the femoral vein. To the catheters in the left groin, a filter prepared according to example 7 and heparinised according to example 8 was connected via a PVC-tubing set. To the catheters in the right groin, a filter of the same size, but with fibres made of non-heparinised, non-aminated cellulose acetate was connected in the same way. All other components in the circuit were heparinised essentially according to EP0086187B2. No external pump was used, thus the driving force was the arterial pressure of the pig. During the experiment, the pressure before and after both filter modules was recorded with a Grass Polygraf. Blood flow through the filter modules was measured with a transonic T101 flowmeter equipped with a clamp-on probe. Because of the large size of the filter modules, the development of blood clots at the in- and outlets could be followed visually. No heparin or other anticoagulants were given during the experiment.

Small blood-clots could be seen at the outlet of the heparinised filter module after 5.5 hours, the flow remaining constant. No clots were observed at the inlet. The experiment was intentionally stopped after 9 hours. The clots had increased somewhat in size and the flow was reduced with 25%. The first blood-clot appeared after 1 hour at the outlet and after 2.5 hours at the inlet of the non-heparinised control filter module. After 3 hours, the blood flow started to decrease rapidly, and after 4 hours it was only 25% of the initial blood-flow. At that point the filter module became completely occluded with blood clots, the flow stopped, and the filter module was removed.

This experiment demonstrates the improved blood-compatibility of a full size hollow fibre hemofiltration module prepared according to the present invention.

EXAMPLE 11

Permeability Studies of Heparinised Hollow Fibre Membranes.

Mini filter units for rat experiments were prepared according to example 7 and heparinised according to example 8. Non-heparinised mini filters without polyethyleneimine in the fibres were prepared according to example 7 for control experiments. Diffusive clearance, ultra filtration rates and sieving coefficients of the mini filters were investigated in anaesthetised and nephrectomized Sprague-Dawley rats essentially using the experimental set up as described in example 9 but giving 100IU of heparin I.V. to the rat immediately before the start of the experiment. The sieving coefficients were 1.0 for urea and creatinine both for the heparinised (n=3) and non-heparinised filters (n=2) and ultrafiltration rates were also similar for both filters. The diffusive transport was studied with respect to clearance of urea, creatinine and inulin in heparinised-(n=4) and non-heparinised (n=3) filters. The mean values ±S.D. for heparinised- and non-heparinised filters were respectively 0.47±0.07 ml/min and 0.44±0.08 ml/min for urea: 0.34±0.08 ml/min and 0.31 ±0.04 ml/min for creatinine and 0.22±0.08 ml/min and 0.16±0.04 ml/min for inulin. In conclusion heparinisation of hollow fibres can be achieved according to the present invention without significantly changing the properties of the fibres with respect to convective and diffusive transport of metabolites.

We claim:

1. A surface-modified non-thrombogenic membrane for use in contact with body fluids or tissue, which comprises
    (a) at least one surface modifying polymer incorporated into the membrane material to give functional groups on the membrane surface; and
    (b) a antithrombotic compound immobilized on the membrane surface by being covalently coupled to said functional groups on the membrane surface.

2. Membrane according to claim 1 wherein the surface modifying polymer comprises the functional groups amine, anhydrido, carboxy, isocyanate, epoxy, carbodiimido, sulfonic acid and hydroxy.

3. Membrane according to claim 2 wherein the surface modifying polymer comprises polyamines, polyanhydrides, polycarboxylic acids, polyisocyanates, polyepoxides, polycarbodiimides, polyalcohols and polysaccharides.

4. Membrane according to claim 1 wherein the membrane material comprises at least one membrane forming polymer.

5. Membrane according to claim 4 wherein the membrane material comprises cellulose, cellulose acetate, polysulfone, sulfonated polysulfone, polyamide, polyacrylonitrile, polymethylmetacrylate or other derivatives thereof.

6. Membrane according to claim 1 wherein the antithrombotic compound is heparin.

7. Membrane according to claim 1 wherein the membrane is a hollow fibre.

8. A method for preparing a surface modified nonthrombogenic membrane with an antithrombotic compound covalently coupled to functional groups on the membrane surface, which comprises the following steps:
   (a) preparing a casting solution including a membrane forming polymer;
   (b) precipitating the membrane forming polymer in a coagulation bath, which coagulation bath comprises at least one surface modifying polymer to form functional groups on the surface of the membrane to which antithrombotic compounds can be covalently coupled; and
   (c) covalently coupling an antithrombotic compound to the functional groups on the surface of the membrane.

9. Method according to claim 8 or 14 wherein the functional groups are selected from the group consisting of amine, anhydrido, caboxy, isocyanate, epoxy, carbodiimido, sulfonic acid and hydroxy groups.

10. Method according to claim 9, wherein the surface modifying polymer is selected from the group consisting of polyamines, polyanhydrides, polycarboxylic acids, polyisocyanates, polyepoxides, polycabodimides, polyalcohol and polysacchrides.

11. Method according claim 8 wherein the membrane material is selected from the group consisting of cellulose, cllulose acetate, polysulfone, sulfonated polysulfone, polyamide, polyacrylonitrile, polymethylacrylate and derivatives thereof.

12. Method according to claim 8 wherein the antithrombotic compound is heparin.

13. Method according to claim 8 wherein the polymeric membrane is a hollow fibre.

14. A method for preparing a surface modified nonantithrombotic membrane with an antithrombotic compound covalently coupled to functional groups on the membrane surface, which comprises the following steps:
   (a) preparing a casting solution including a membrane forming polymer and at least one surface modifying polymer;
   (b) precipitating the membrane from a coagulation bath to form a membrane having functional groups on its surface; and
   (c) covalently coupling an antithrombotic compound to the functional groups on the surface of the membrane.

* * * * *